United States Patent [19]
Li et al.

[11] Patent Number: 5,880,115
[45] Date of Patent: Mar. 9, 1999

[54] STEROID SULFATASE INHIBITORS AND METHODS FOR MAKING AND USING THE SAME

[75] Inventors: Pui-Kai Li, Library; Kyle W. Selcer, Export, both of Pa.

[73] Assignee: Duquesne University of the Holy Ghost, Pittsburgh, Pa.

[21] Appl. No.: 897,247

[22] Filed: Jul. 18, 1997

[51] Int. Cl.$^6$ ............... A61K 31/56; C07J 3/00; C07J 41/00

[52] U.S. Cl. ........... 514/169; 514/182; 552/522; 552/611

[58] Field of Search ............... 552/522, 611; 514/169, 182

[56] References Cited

U.S. PATENT DOCUMENTS

| | | | |
|---|---|---|---|
| 5,556,847 | 9/1996 | Johnson et al. | 514/178 |
| 5,567,831 | 10/1996 | Li | 554/43 |
| 5,571,933 | 11/1996 | Li et al. | 552/521 |
| 5,616,574 | 4/1997 | Reed et al. | 514/178 |

FOREIGN PATENT DOCUMENTS 86393  12/1971  Germany.

OTHER PUBLICATIONS

Howarth et al., "Phosphonates and Thiophosphonates As Sulfate Surrogates: Synthesis of Estrone 3–Methylthiophosphonate, A Potent Inhibitor of Estrone Sulfatase", *Bioorg. Med. Chem. Lett.*, vol. 3, pp. 313–318 (1993).

Duncan et al., "Inhibition of Estrone Sulfatase Activity by Estrone–3–methylthiophosphonate: A Potential Therapeutic Agent in Breast Cancer", *Cancer Res.*, vol. 53, pp. 298–302 (Jan. 15, 1993).

Li et al., "Synthesis and biochemical studies of estrone sulfatase inhibitors", *Steroids*, vol. 58, pp. 106–111 (Mar. 1993).

Dibbelt et al., "Inhibition of Human Placental Sterylsulfatase by Synthetic Analogs of Estrone Sulfate", *J. Steroid Biochem. Molec. Biol.*, vol. 50, No. 5/6, pp. 261–266 (1994).

Howarth et al., "Estrone Sulfamates: Potent Inhibitors of Estrone Sulfatase with Therapeutic Potential", *J. Med. Chem.*, vol. 37, pp. 219–221 (1994).

Purohit et al., "In Vivo Inhibition of Oestrone Sulphatase and Dehydroepiandrosterone Sulphatase By Oestrone–3–O–Sulphamate", *Int. J. Cancer*, vol. 63, pp. 106–111 (1995).

Li et al., "Estrone sulfate analogs as estrone sulfatase inhibitors", *Steroids*, vol. 60, pp. 299–306 (1995).

Selcer et al., "Inhibition of Placental Estrone Sulfatase Activity and MCF–7 Breast Cancer Cell Proliferation by Estrone–3–amino Derivatives", *J. Steriod Biochem. Molec. Biol.*, vol. 59, No. 1, pp. 83–91 (1996).

*Primary Examiner*—José G. Dees
*Assistant Examiner*—Barbara Badio
*Attorney, Agent, or Firm*—Diane R. Meyers; Arnold B. Silverman; Eckert Seamans Cherin & Mellott, LLC

[57] ABSTRACT

Sulfatase inhibitor compounds having the formula:

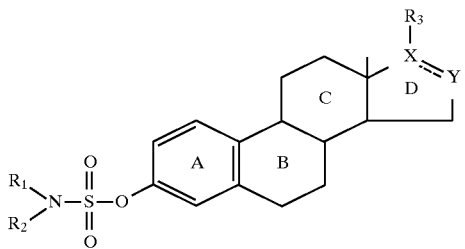

wherein X, Y, $R_1$, $R_2$ and $R_3$ are as defined in the specification. The compounds are useful in the treatment of estrogen dependent illnesses. Methods for synthesizing these compounds are also disclosed.

18 Claims, 7 Drawing Sheets

STEROID SULFATASE INHIBITORS AND METHODS FOR MAKING AND USING THE SAME

BACKGROUND OF THE INVENTION

1. Field of the Invention

The present invention relates to sulfatase inhibitors and methods for making and using the same. These methods include use of these compounds in therapeutic and prophylactic treatments for estrogen dependent illnesses.

2. Background Information

Estrogen levels in breast tumors of post-menopausal women are at least ten times higher than estrogen levels in plasma. The high levels of estrogen in these tumors are due to in situ formation of estrogen, possibly through conversion of estrone sulfate to estrone by the enzyme estrone sulfatase. Inhibitors of estrone sulfatase are therefore potential agents for the treatment of estrogen-dependent breast cancers. Most estrone sulfatase inhibitors are steroidal in nature. Although estrone-3-O-sulfamate (EMATE) is believed to be the most potent inhibitor of estrone sulfatase, recent evidence indicates that this compound is a potent estrogen. This compound is therefore not useful in the treatment of estrogen dependent illnesses.

Reed and co-workers reported on sulfatase inhibitory activities of estrone-3-O-methylthiophosphonate, estrone-3-O alkyl and aryl sulfonates, estrone-3-O-phosphonates and thiophosphonates and estrone sulfamates in: Duncan et al., "Inhibition of estrone sulfate activity by estrone-3-methylthiophosphonate", Cancer Res. 53:298–303 (1993); Howarth et al., "Phosphonates and thiophosphonates as sulfate surrogates: Synthesis of estrone-3-methylthiophosphonate, a potent inhibitor of estrone sulfatase", Bioorg. Med. Chem. Lett. 3:313–318 (1993); Howarth et al., "Estrone sulfamates: Potent inhibitors of estrone sulfatase with therapeutic potential", J. Med. Chem. 37:219–221 (1994); and Purohit, et al., "In vivo inhibition of Oesterone Sulphatase and Dehydoepiandrosterone Sulphatase by Oestrone-3-O-sulphamate", Int. J. Cancer, 63:106–111 (1995).

Li and co-workers reported the synthesis and sulfatase inhibitory activities of sulfonate and its analogues, methylene sulfonates and phosphate that contain the estrone nucleus in Li et al., "Synthesis and biochemical studies of estrone sulfatase inhibitors", Steroids, 58:106–111 (1993); Dibbelt et al, "Inhibition of human placental sterylsulfatase by synthetic analogues of estrone sulfate", J. Steroid Biochem. Molec. Biol., 52 (3):281–286 (1995); and Li et al., "Estrone sulfate analogues as estrone sulfatase inhibitors", Steroids 60:299–306 (1995). Estrone-3-amino derivatives are reported in Selcer et al., "Inhibition of Placental Estrone Sulfatase Activity and MCF-7 Breast Cancer Cell Proliferation by Estrone-3-amino Derivatives", J. Steroid Biochem. Molec. Biol., 59:83–91 (1996).

U.S. Pat. No. 5,567,831 is directed to the use of non-steroidal sulfatase inhibitor compounds in the treatment of estrogen dependent illnesses.

U.S. Pat. No. 5,571,933 is directed to derivatives of estra 1,3,5(10)triene-17-one, 3-amino compounds and methods for using these compounds in the treatment of estrogen dependent illnesses.

U.S. Pat. No. 5,556,847 is directed to steroidal sulfatase inhibitors and methods for using these inhibitors to effect memory enhancement. Use of these inhibitors in the treatment of estrogen dependent illnesses is not disclosed.

U.S. Pat. No. 5,616,574 discloses steroid sulphatase inhibitors and the methods of using the same. The disclosed compounds do not include the C17 substituted 1,3,5,(10) triene compounds of the present invention. The compounds are potent estrogens and metabolize to form estrones, which further distinguishes them from the compounds of the present invention which do not metabolize to form estrones.

There remains a need, therefore, for potent sulfatase inhibitors that are metabolically stable, more selective and devoid of estrogenic activity.

SUMMARY OF THE INVENTION

The present invention has met the above described needs by providing compounds useful as steroid sulfatase inhibitors. These compounds have the general formula:

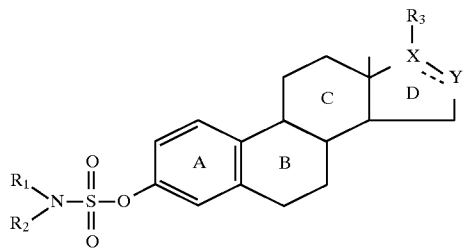

wherein $R_1$ and $R_2$ are independently selected from the group consisting of hydrogen and a lower alkyl group having between about one and six carbons;
wherein $R_3$ is selected from the group consisting of

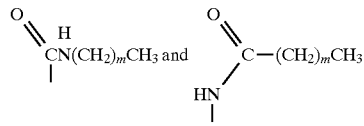

wherein m is between about 3 and 13;
wherein X and Y are both carbons and the bond between X and Y is either single or double, except when

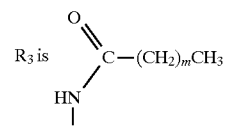

the bond between X and Y is single;
and
wherein the ring system ABCD is a steroid nucleus, more specifically an estrone, most specifically a 1,3,5(10) triene. Suitable steroid ring systems within the scope of the present invention include, but are not limited to:

Substituted estrones as follows:
2-OH-estrone
2-methoxy-estrone
4-OH-estrone
6 alpha-OH-estrone
7 alpha-OH-estrone
16 alpha-OH-estrone
16 beta-OH-estrone
Other suitable estrone compounds that function in the manner described herein are also within the scope of the present invention.

Preferably, $R_1$ and $R_2$ are both hydrogen,

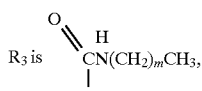

the bond between X and Y is single and m is between about 6 and 9. Most preferably, m is equal to 6.

The present invention is also directed to methods for synthesizing these compounds, which generally involve reacting an estrone with an amine.

In addition, the present invention relates to methods for using these compounds as sulfatase inhibitors. These methods generally comprise incorporating one or more of the compounds into a suitable pharmaceutical carrier and administering a therapeutically or prophylactically effective amount of the compound to a patient.

It is an object of this invention to provide compounds for substantially inhibiting the steroid sulfatase enzyme produced in the body.

It is a further object of the invention to provide estrone sulfatase inhibitor compounds having anti-tumor or synergistic activity with anti-estrogen and aromatase inhibitors.

It is a further object of the present invention to provide estrone sulfatase inhibitor compounds providing effective activity against estrogen dependent illnesses.

Yet another object of the invention is to provide methods for therapeutically or prophylactically treating a patient with the sulfatase inhibitor compounds of the present invention.

It is another object of this invention to provide derivatives of sulfatase inhibitor compounds that are not metabolized to compounds that are estrogenic.

These and other objects of the invention will be more fully understood to those skilled in the art upon review of the following description and appended claims.

DETAILED DESCRIPTION OF THE INVENTION

As used herein, the term "patient" refers to members of the animal kingdom including but not limited to human beings.

The present invention relates to compounds having the formula:

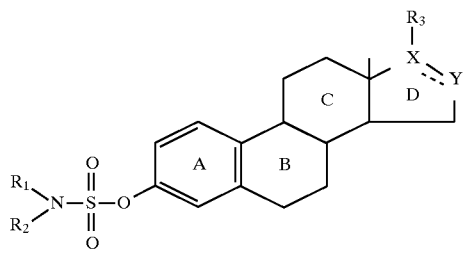

wherein $R_1$ and $R_2$ are independently selected from the group consisting of hydrogen and a lower alkyl group having between about one and six carbons;
wherein $R_3$ is selected from the group consisting of

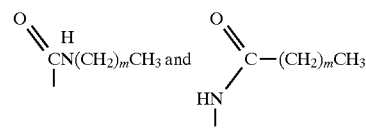

wherein m is between about 3 and 13;
wherein X and Y are both carbons and the bond between X and Y is either single or double, except when

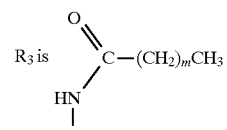

the bond between X and Y is single;
and
wherein the ring system ABCD is a steroid nucleus. As will be appreciated by those skilled in the art, the compounds of the present invention are estrones, more particularly 1,3,5 (10) trienes. Suitable steroid ring systems include the substituted estrones:
  2-OH-estrone
  2-methoxy-estrone
  4-OH-estrone
  6 alpha-OH-estrone
  7 alpha-OH-estrone
  16 alpha-OH-estrone
  16 beta-OH-estrone Preferably, $R_1$ and $R_2$ are both hydrogen,

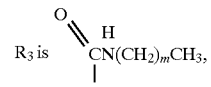

the bond
between X and Y is single, and m is between about 6 and 9. Most preferably, m is equal to about 6.

The compounds of the present invention are useful as sulfatase inhibitors. These compounds include a membrane insertion region (a long alkyl chain attached at C17) and a steroid nucleus and function as active-site directed irreversible inhibitors of estrone sulfatase. The steroidal molecule released after inactivation of the enzyme is not estrogenic.

Figure 1:
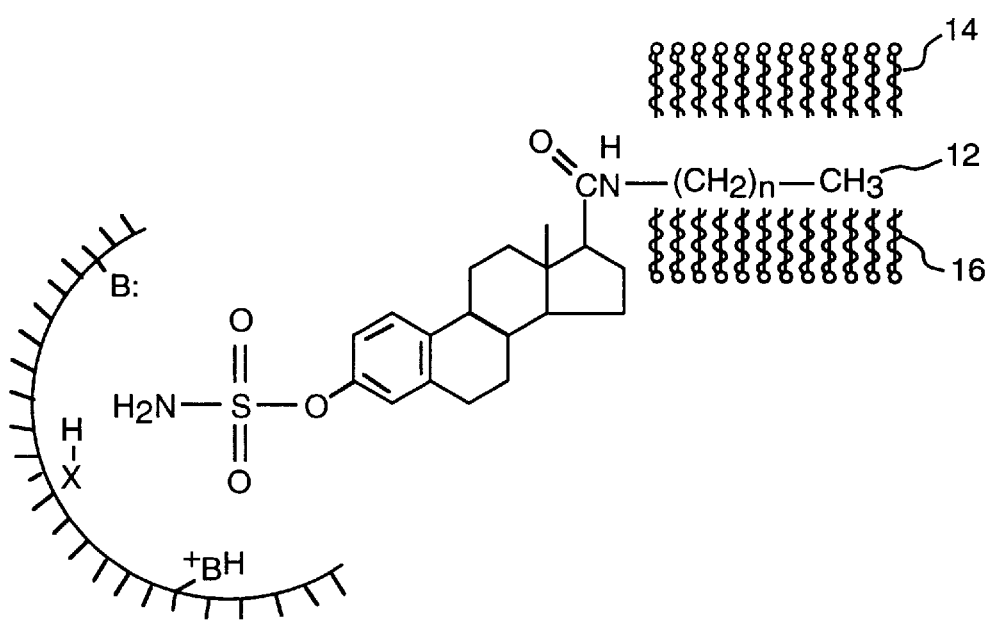
FIG. 1 illustrates the manner in which the C17 alkyl chain substituent fits into a lipid bilayer.

Since estrone sulfatase is a membrane bound enzyme, the long alkyl chain substitutes on C17 of the estrone nucleus serves to further anchor the compound into the membrane. As illustrated in FIG. 1, the long alkyl chain (12) is inserted between the two layers (14 and 16) of the lipid bilayer of a membrane. Hydrophobic interaction keeps the chain within the bilayer. This additional binding site results in more potent sulfatase inhibitory activity.

The present invention is further directed to the synthesis of the above-described compounds. This synthesis generally includes treating estrone with an amine. More specifically, the synthesis of the sulfatase inhibitor compounds 6a–6d of the present invention are summarized in FIG. 2. Estrone(1) is used as the starting material, and is converted to bis-triflate(2) by the procedure reported by Holt et al., "Steroidal A ring aryl carboxylic acids: A new class of steroidal Sa-reductase inhibitors", *J. Med. Chem.* 33:937–942 (1990). The greater propensity for Pd insertion into the vinyl triflate over the aryl triflate allows for the chemoselective introduction of the D ring carboxamide. By using different aliphatic amines wherein m is between 3 and 13, more preferably between 6 and 9, amides 3a–d are obtained. Cleavage of the aryl triflate of 3a–d by treatment with $K_2CO_3$ in a mixture of MeOH—$H_2O$ (9:1) at reflux affords phenols 4a–d which can be converted to the corresponding sulfamates 5a–d by standard methods such as those disclosed by Howarth et al., "Estrone sulfamates: Potent inhibitors of estrone sulfatase with therapeutic potential", *J. Med. Chem.* 37:219–221 (1994). Hydrogenation of α,β unsaturated amides furnishes compounds 6a–d in high yield.

Figure 2:
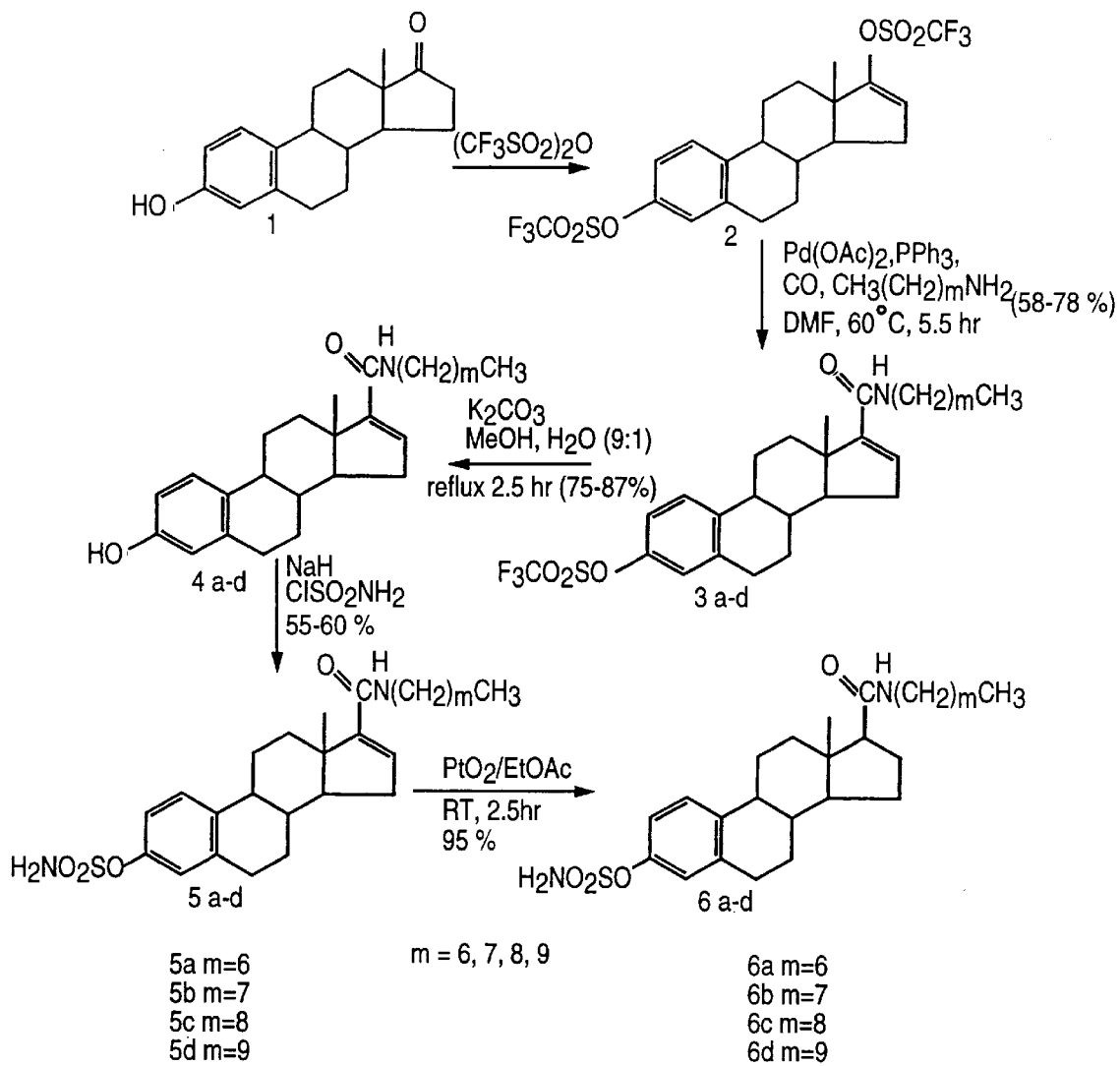
FIG. 2 illustrates the scheme for preparing compounds according to the methods of Example 1.
Figure 3:
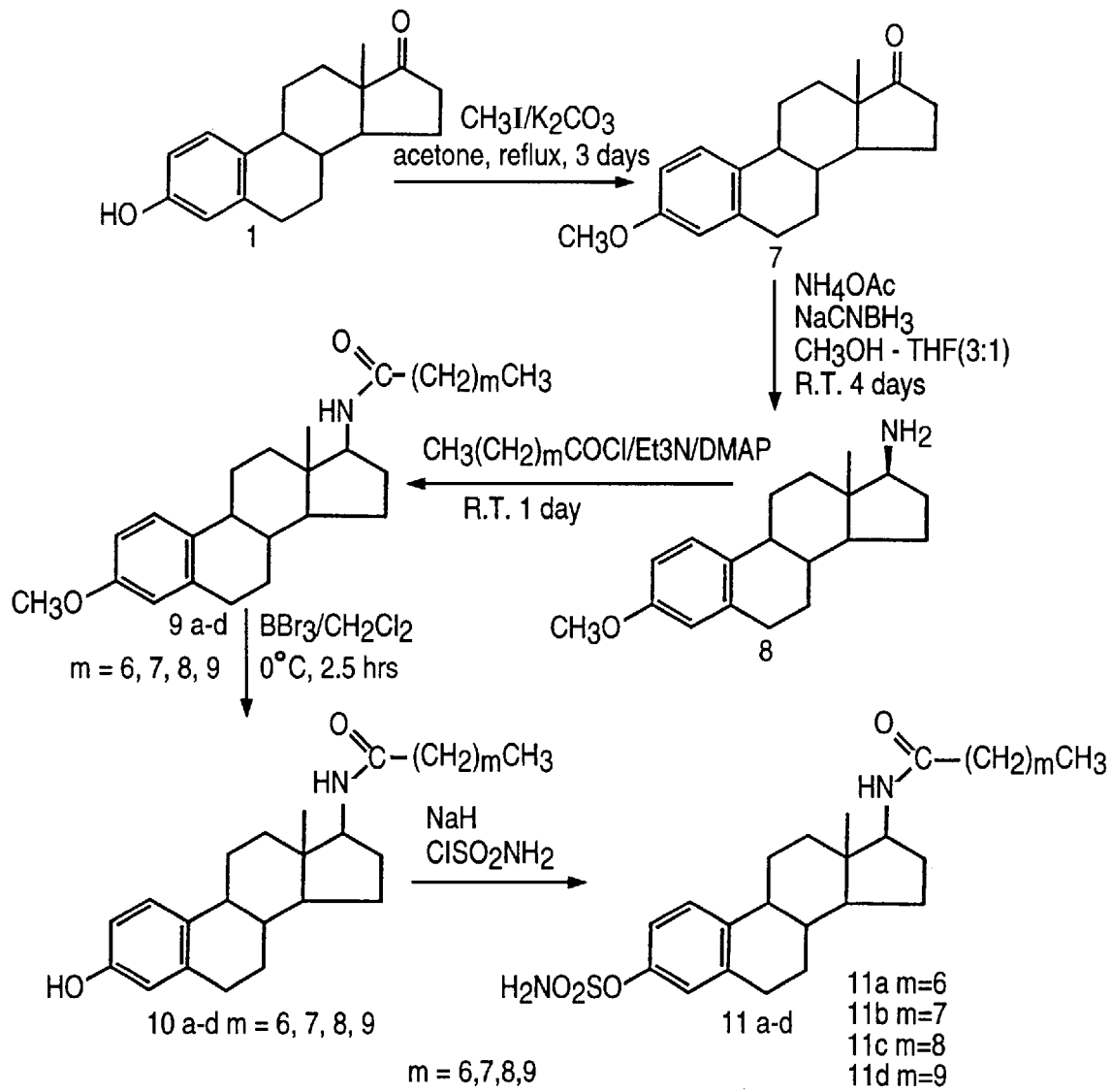
FIG. 3 illustrates the scheme for preparing compounds according to the methods of Example 2.

FIG. 3 outlines the synthesis of the reverse analogue of compounds 6a–d. Compounds 11a–d are designed through reversing the amide bonds of compounds 6a–d (shown in FIG. 2). Methylation of estrone (1) with methyl iodide followed by reductive amination of 3-methoxy-estra-1,3,5 (10)triene-17-one (7) gives the 17β-amino compound (8). Treatment of amine (8) with one of various aliphatic carboxylic acid chlorides affords the corresponding amides 9a–d based on the crude amine (8). Cleavage of methyl ether of compounds 9a–d with $BBr_3$ yields phenols 10a–d which are sulfamoylated, leading to the final compounds 11a–d.

As used herein, compounds referred to with the designation "a" have m equal to 6, "b" have m equal to 7, "c" have m equal to 8 and "d" have m equal to 9.

The present invention is further directed to methods for using the compounds described above to therapeutically and/or prophylactically treat a patient for an estrogen dependent illness. Such illnesses include, but are not limited to, breast cancer, vaginal cancer, endometrial cancer, ovarian cancer and endometriosis. Use of other suitable substituted estrones is also within the scope of these methods; suitable substituted estrones include estrones having sulfatase inhibition activity and long alkyl chains at C17 that can be incorporated into a lipid bilayer.

The methods of the present invention include the steps of: a) incorporating the compounds of the present invention in a suitable pharmaceutical carrier; and b) administering either a therapeutically effective dosage or a prophylactically effective dosage of the compounds incorporated in the carrier to a patient.

Any suitable pharmaceutical carrier can be used, so long as compatibility problems do not arise. A preferred pharmaceutical carrier is physiologic saline (0.9% sodium chloride), 95% dextrose in water.

Administration of an effective dosage to a patient can be accomplished by parenteral injection, such as intravenously, intrathecally, intramuscularly or intra-arterially. The compounds can also be administered orally or transdermally, or by any other means known to those skilled in the art. Oral administration is preferred.

As used herein, the term "therapeutically effective amount" refers to that amount of one or more of the compounds of the present invention required to therapeutically treat a patient. Similarly, the term "prophylactically effective amount" refers to that amount of one or more of the compounds of the present invention needed to prophylactically treat a patient.

As will be appreciated by those skilled in the art, the dosage of compound given, the route of administration and the duration of therapy will be dependent upon the individual being treated, taking into consideration such factors as the particular estrogen dependent illness being treated, the body weight of the patient, other therapies being employed to treat the patient, and the condition, clinical response and tolerance of the patient. Dosage, administration, and duration of therapy can be determined by one skilled in the art upon evaluation of these and similar factors. A typical patient will be a post-menopausal female or pre-menopausal female who has been ovariectomized. Although the dosage and administration will vary from patient to patient, a typical dose will range between 1 mg and 2 mg per kg of body weight, and will be administered daily.

EXAMPLES

The following examples are intended to illustrate the invention and should not be construed as limiting the invention in any way.

For all of the examples, chemicals and silica gel were purchased from Aldrich Chemical Company (Milwaukee, Wis.). The chemicals were checked for purity by thin layer chromatography and NMR. Biochemicals, estrone and estrone sulfate were obtained from Sigma Chemical Company (St. Louis, Mo.). [6,7-$^3$H]Estrone sulfate was purchased from Dupont Company. Melting points were determined on a Thomas Hoover capillary melting point apparatus and were uncorrected. Proton NMR spectra were obtained with a Bruker WH-300 (300 MHz) spectrophotometer. Elemental analyses were performed by Atlantic Microlab Inc. (Norcross, Ga.). Radioactive samples were analyzed with a Packard Tri-Carb 4530 Liquid Scintillation Counter. The liquid scintillation cocktail was Ecolume (ICN, Costa Mesa, Calif.).

Example 1

Reference numerals correspond with those shown in FIG. 2. For all of the "a" compounds discussed in the examples, m=6, for the "b" compounds m=7, for the "c" compounds m=8 and for the "d" compounds m=9. The methods described in this example relate to synthesis of "a" compounds. These methods can be easily modified to prepared "b", "c" and "d" compounds by use of $CH_3(CH_2)_7NH_2$, $CH_3(CH_2)_8NH_2$ and $CH_3(CH_2)_9NH_2$, respectively, instead of $CH_3(CH_2)_6NH_2$.

Synthesis of 3-[(trifluoromethyl)sulfonyl]oxy-17-(N-heptylcarbamoyl)estra-1,3,5(10),16-tetraene (3a).

Compound 1 was mixed with $(CF_3SO_2)_2O$ to yield bis-triflate (2). A mixture comprising about 1.8 g of bis-triflate (2), about 68 mg of Palladium (II) acetate and about 143 mg of triphenylphosphine and n-heptylamine ($CH_3(CH_2)_6NH_2$, 10 ml) in dimethylformamide (DMF, 15 ml) was heated at 60° C. with carbon monoxide bubbled through for 5.5 h. The reaction mixture was then diluted with methylene chloride ($CH_2Cl_2$) and washed with 10% aqueous hydrochloric acid (HCl), 10% aqueous sodium bicarbonate ($NaHCO_3$) and brine. The organic layer was dried sodium sulfate ($Na_2SO_4$), concentrated and the residue was purified by chromatography on silica gel (petroleum ether: ethyl acetate (EtOAc), 4:1), yielding the pure α-β-unsaturated amide (3a) (58%).
Synthesis of 3-Hydroxy-17-(N-heptylcarbamoyl) estra-1,3, 5(10),16-tetraene (4a).

About 2.05 g of compound 3a (m=6) was dissolved in a mixture of methanol (90 ml) and water (10 ml). About 1.6 g of solid potassium carbonate ($K_2CO_3$) was added and the reaction mixture was refluxed for 2.5 h. After removal of most of the methanol, 50 ml of 1N HCl was added to the reaction mixture. The precipitate formed was filtered and washed with water, yielding the phenol 4a (1.34 g, 87%).
Synthesis of 3-Sulfamoyloxy-17-(N-heptylcarbamoyl)-estra-1,3,5(10),16-tetraene (5a).

About 29.6 mg of sodium hydride was added to a solution comprising about 250 mg of compound 4a in about 20 ml of anhydrous DMF at 0° C. under nitrogen. The solution was stirred for 30 minutes and about 1.22 g of chlorosulfonamide was slowly added in one portion. The solution was then stirred at room temperature for 24 hours. The mixture was poured into a cold saturated sodium bicarbonate solution and the resulting solution was extracted with methylene chloride (3×50 ml). The organic layer was separated, dried ($Na_2SO_4$) and concentrated under reduced pressure to give a light yellow oil (5a) (183 mg 61.2%).
Synthesis of 3-Sulfamoyloxy-17β-(N-heptylcarbamoyl) estra-1,3,5(10)-triene (6a).

A solution comprising about 210 mg of compound 5a (m=6) in about 6 ml of EtOAc and about 2 ml of ethanol (EtOH, 2 ml) was stirred over about 40 mg of platinum (IV) oxide ($PtO_2$) under an atmosphere of hydrogen for 2.5 h. The catalyst was removed by filtration and the filtrate concentrated. The residue was purified by silica gel chromatography (Petroleum ether: EtOAc, 1:1), yielding pure compound 6a (201 mg, 95.3%).

Example 2

Reference numerals correspond with those shown in FIG. 3. For all of the "a" compounds m=6, for the "b" compounds m=7, for the "c" compounds m=8, and for the "d" compounds m=9. The methods described herein relate to synthesis of "a" compounds. These methods can be easily modified to prepared "b", "c" or "d" compounds by use of $CH_3(CH_2)_7COCl$, $CH_3(CH_2)_8COCl$ or $CH_3(CH_2)_9COCl$, respectively, instead of $CH_3(CH_2)_6COCl$.
Synthesis of 3-methoxy-17β-octanoylamino-estra-1,3,5(10) -triene (9a).

Compound 1 is mixed with $CH_3I/K_2CO_3$ and acetone and refluxed for 3 days to yield compound 7. A solution comprising about 8.9 g of compound 7 and about 24 g of ammonium acetate ($NH_4OAc$) in 675 ml of tetrahydrofuran (THF) and 225 ml of MeOH was prepared to which was added 3.7 g of sodium cyanoborohydride ($NaCNBH_3$). The reaction mixture was stirred at room temperature for 4 days. The mixture was poured into 3 L of a chilled 5 % $NaHCO_3$ solution. Precipitates were collected by filtration and dried under vacuum, giving 8.2 g (91.8%) of crude product, compound 8, which was used directly for the next acylation reaction without purification.

To a chilled solution comprising about 2 g of crude 8, about 2.2 ml of triethylamine ($Et_3N$) and about 172 mg 4-dimethyamino pyridine (DMAP) in 60 ml of $CH_2Cl_2$ was added 2.3 ml of octanoyl chloride. The reaction mixture was stirred at room temperature overnight and washed with saturated $NaHCO_3$ (2×30 ml) and water (30 ml), and dried with $Na_2SO_4$. Evaporation of the solvent and the residue was purified by silica gel chromatography (Petroleum ether—EtOAc, 3:2), yielding compound 9a (m=6).

Synthesis of 3-hydroxy-17β-octanoylamino-estra-1,3,5(10) -triene (10a).

To a solution comprising about 1.3 g of compound 9a (m=6) in 50 ml of $CH_2Cl_2$ was added 7.0 ml of boron tribromide ($BBr_3$, 1M solution in $CH_2Cl_2$) at 0° C. under nitrogen atmosphere. The reaction mixture was stirred at 0° C. for 2.5 h and quenched by adding about 30 ml of 1N HCl. The organic layer was separated and the aqueous layer was extracted with $CH_2Cl_2$ (2×30 ml). The combined organic layer was dried with $Na_2SO_4$ and concentrated in vacuo. The residue was purified by silica gel chromatography (petroleum ether: EtOAc, 1:1) affording the phenol 10a (1.1 g, 88%).
Synthesis 3-sulfamoyloxy-17β-octanoylamino-estra-1,3,5 (10)-triene (11a).

Sulfamates 11a (50%) were prepared by using the procedure outlined in Example 1 for the synthesis of sulfamate (5a), but using compound 10a instead of compound 4a.

Example 3

The compounds prepared in Examples 1 and 2 were tested for biological activity in inhibiting sulfatase activity using an in vitro conversion assay procedure. As will be appreciated by those skilled in the art, this assay is based on inhibition of the conversion of $^3$H-estrone sulfate to $^3$H-estrone by the enzyme estrone sulfatase in intact breast cancer cell cultures. Cells are incubated in the presence of $^3$H-estrone sulfate with or without estrone sulfatase inhibitors. In the absence of inhibitors, the cells convert the $^3$H-estrone sulfate to $^3$H-estrone, which may be converted by the cells to $^3$H-estradiol. The unconjugated tritiated estrogens (estrone and estradiol) are then extracted from the cell culture medium using toluene and quantitated by liquid scintillation counting. In the presence of estrone sulfatase inhibitors, the conversion of estrone sulfate to unconjugated estrogens is significantly reduced or eliminated.

MDA-MB-231 cells were obtained from the American Type Culture Collection (Bethesda, Md.). All cell culture media and reagents were purchased from Sigma Chemical Co. (St. Louis, Mo.). Growth medium, used for routine growth of breast cancer cells, was RPMI-1640 medium containing 0.2% (v/v) sodium bicarbonate, 5% heat-inactivated fetal calf serum, 10 mg/ml gentamycin, 1% (v/v) antibiotic/antimycotic, 5 mg/ml amphotericin B. Serum-free medium contained all of the components mentioned above except fetal calf serum. Estrogen-free medium contained RPMI-1640 phenol-red-free medium, 5% dextran-coated-charcoal-stripped fetal calf serum, 0.5 mM L-glutamine, 0.2% (v/v) sodium bicarbonate, 10 mg/ml gentamycin, 1% (v/v) antibiotic/antimycotic, and 5 mg/ml amphotericin B.

The ability of the estrone sulfatase inhibitors prepared in Examples 1 and 2 to block hydrolysis of estrone sulfate was examined using intact monolayers of MDA-MB-231 cells. Cells (1×10$^6$) were seeded into 6-well plates and incubated in growth medium overnight to allow them to adhere. After incubation, the medium was replaced with 2 ml of serum-free medium containing $^3$H-estrone sulfate (75,000 dpm/ml) with or without experimental compounds in concentrations ranging between about 0.025 nM to 2.5 nM as indicated below. After 18 h of incubation, the plates were cooled and 0.5 ml of medium was pipetted into each of two 16×100 mm tubes. Three ml of toluene was added to each tube for extraction of unconjugated steroids. The mixture was vortexed for 1 minute and then centrifuged for 5 minutes to separate the aqueous and organic phases. One ml of organic phase (containing $^3$H-labeled unconjugated steroids) was transferred to a scintillation vial and 5 ml of liquid scintillation cocktail was added. Radioactivity was counted in a Packard Tri-carb scintillation counter at 50% efficiency for $^3$H. Product formation for samples containing inhibitors were compared to those of the control samples (no inhibitor). Data are typically expressed as percent of control.

Figure 4:
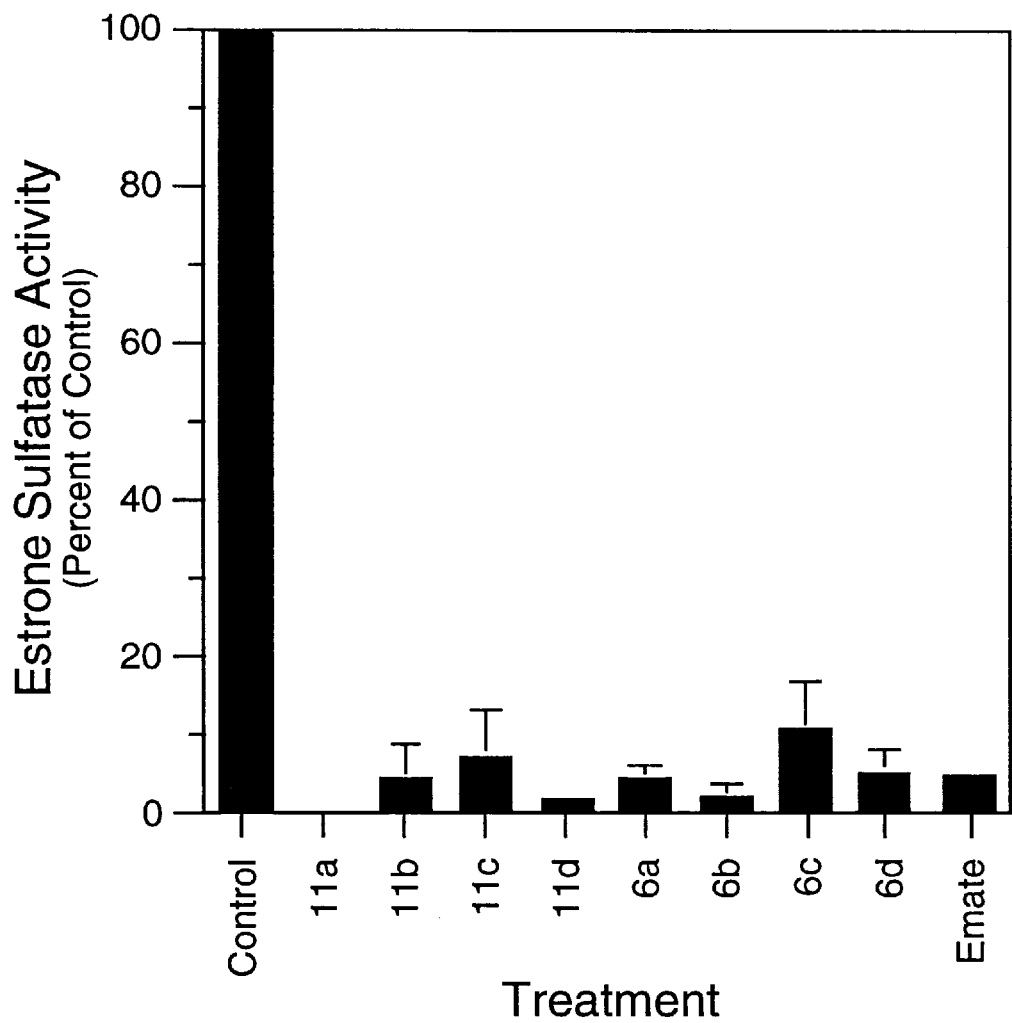
FIG. 4 illustrates inhibition of estrone sulfatase activity by compounds 6a–d and 11a–d and a control, as determined by an in vitro conversion assay of intact human breast cancer cells determined according to the methods of Example 3. Bars represent mean % of control +1 standard error.
Figure 5:
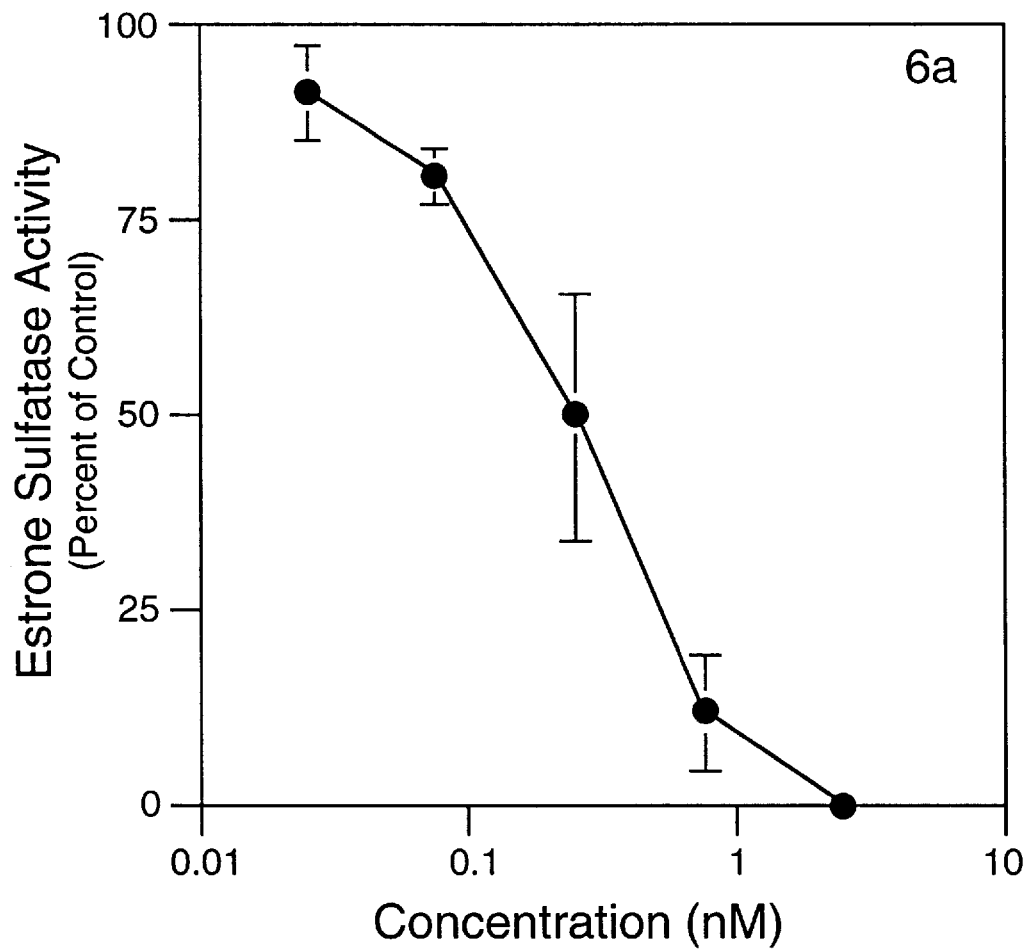
FIG. 5 illustrates dose-dependent inhibition of estrone sulfatase activity by compound 11a, as determined by an in vitro conversion assay of intact human breast cancer cells determined according to the methods of Example 3. Points represent mean % of control ±1 standard error.
Figure 6:
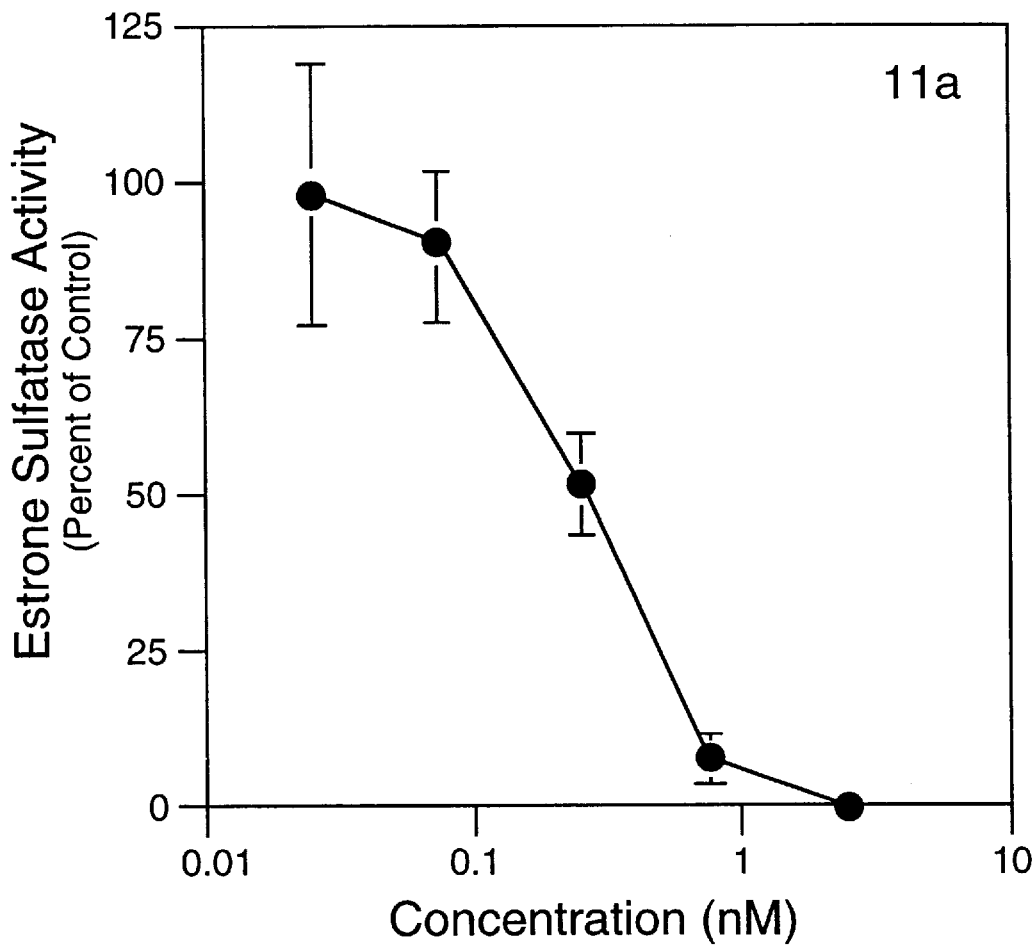
FIG. 6 illustrates dose-dependent inhibition of estrone sulfatase activity by compound 6a, as determined by an in vitro conversion assay of intact human breast cancer cells determined according to the methods of Example 3. Points represent mean % of control ±1 standard error.

Results of the in vitro conversion assay are shown in FIGS. 4–6. FIG. 4 provides a comparison of selected compounds versus the control at a single concentration. Inhibitors were tested in the in vitro conversion assay at a concentration of 2.5 nM to assess the relative potency of the various compounds. The known estrone sulfatase inhibitor estrone sulfamate (EMATE) was included as a reference. Each compound was tested in duplicate in three separate experiments. All of the compounds (6a–d and 11a–d) significantly inhibited estrone sulfatase activity below control levels. Further, the level of inhibition was similar to or exceeded that of estrone sulfamate.

FIGS. 5 and 6 provide dose-response analysis of two representative compounds (6a and 11a). One inhibitor from each series (6a and 11a) was tested over a range of concentrations (0.025 to 2.5 nM) for determination of dose-responsiveness and for calculation of IC$_{50}$ values. The estrone sulfatase activity for compound 11a is shown in FIG. 5, and for compound 6a is shown in FIG. 6. Each concentration was tested in duplicate in three separate experiments. Both compounds showed dose-dependent inhibition of estrone sulfatase activity as determined by the in vitro conversion assay. The IC$_{50}$ values, representing the concentration that resulted in 50% inhibition of estrone sulfatase activity in this assay, were calculated to be 0.425 nM for 11a and 0.450 nM for 6a. The IC$_{50}$ values were determined by performing linear regression analysis of percent of control versus concentration (log10); the resulting equation was then used to determine the concentration that resulted in 50% inhibition.

The data from the in vitro conversion assays as shown in FIGS. 4–6 indicate that the compounds of the present invention are highly potent in their abilities to inhibit estrone sulfatase activity in cultures of human breast cancer cells. Eight of the compounds were shown to substantially and significantly inhibit estrone sulfatase activity at a 2.5 nM concentration. Two compounds, 6a and 11a, were tested over a range of concentrations and found to be dose-responsive. The IC$_{50}$ values of these compounds were in the 0.5 nM range. Results on estrone sulfatase inhibition from the in vitro conversion assay are strongly correlated with results from two other measures of estrone sulfatase inhibition, namely inhibition of human placental microsome estrone sulfatase activity and inhibition of growth of estrogen-dependent human breast cancer cells stimulated by estrone sulfate. Thus, the in vitro conversion assay is a reliable indicator of a compound's ability to inhibit estrone sulfatase activity. Data from this assay indicate that the newly developed compounds are among the most potent estrone sulfatase inhibitors discovered to date.

Example 4

MCF-7 Cell Proliferation Assay to Test for Estrogenicity

A cell proliferation assay was performed to test the ability of compounds to stimulate proliferation of estrogen-dependent MCF-7 cells. MCF-7 cells were seeded into 96-well plates in growth medium (50,000 cells per well). The growth medium was necessary for the cells to adhere properly to the plates. After 24 h, the medium was changed to estrogen-free medium and the cells were incubated for five days, with the medium being changed every two days. This step allowed for estrogen depletion from the cells. After the 5 day period, the medium was changed to estrogen-free medium plus the experimental compounds (1 μM). The cells were incubated for 7 days, with the medium being changed every two days. Two sets of control wells were included in each experiment. Negative control wells were the same as experimental wells, except that after day 5 they were continued on estrogen-free medium alone. These wells represented the number of cells in the absence of stimulation of cell proliferation. Positive control wells were the same as experimental wells except that they contained a known estrogenic agent (estrone). These wells represented estrone stimulation of cell proliferation. On the last day of the experiment, cells were counted using an MTT (3-[4,5-dimethylthiazol-2-yl]-2,5-diphenyltetrazolium bromide; Sigma Chemical Co.) assay. The MTT assay depends on metabolic activity of the cells, and therefore counts living, intact cells. Twenty μl of MTT solution (5 mg/ml in phenol-red-free RPMI-1640 medium) were added to each well of a 96-well plate containing cells and then incubated for 3 hrs at 37° C. At the end of the incubation period, the medium was removed and the converted dye was solubilized with 100 μl acidic isopropanol (0.05 N HCl in absolute isopropanol). Absorbance of converted dye was measured at a wavelength of 570 nm with background subtraction at 690 nm using a BioRad Model 3550 Microtiter Plate Reader. To generate a standard curve, MCRF-7 cells were plated at known densities and allowed to adhere overnight prior to counting by MTT assay. Absorbance of converted dye corresponded linearly to the number of cells.

Figure 7:
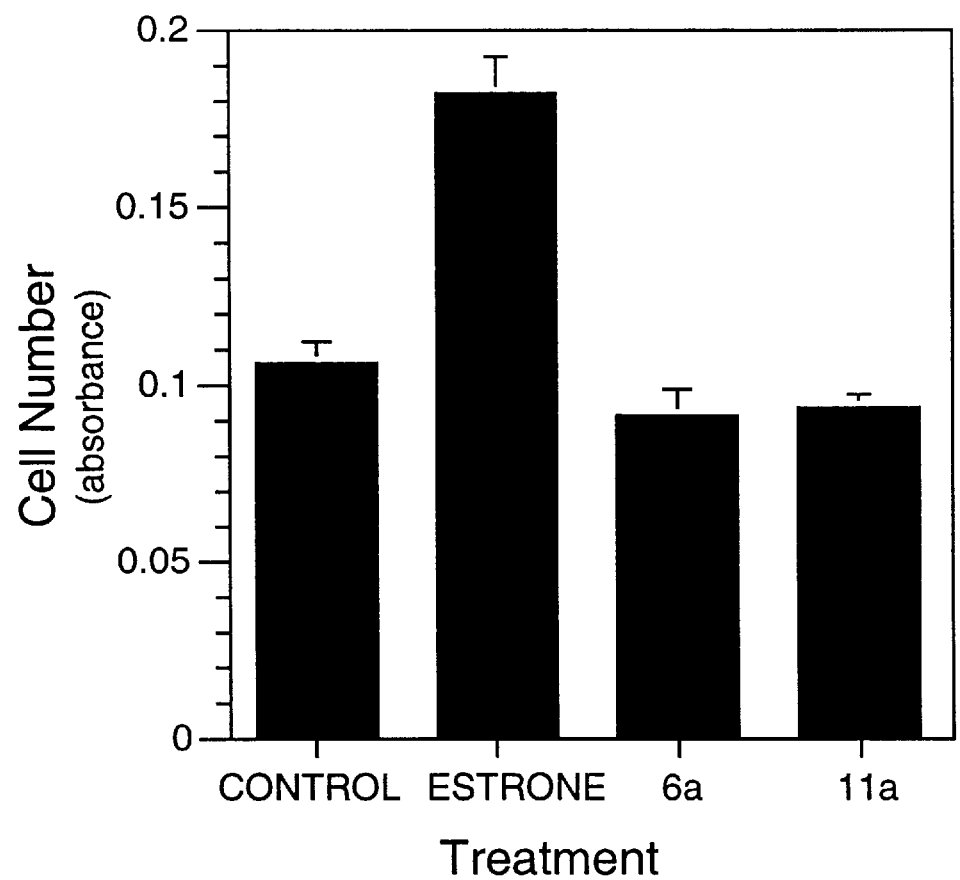
FIG. 7 illustrates the estrogenicity of the compounds of the present invention using an MCF-7 cell proliferation assay, determined according to the methods of Example 4.

The experimental compounds 6a and 11a were tested for estrogenicity using the MCF-7 cells proliferation assay (FIG. 7). Neither compound stimulated cell proliferation at the 1 μM concentration used for the treatments. In contrast, estrone significantly stimulated cell proliferation. These findings indicate that neither compound is estrogenic, even when present at concentrations that are 2000 times greater than their IC$_{50}$ values.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having the formula:

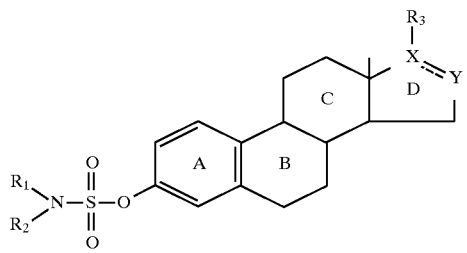

wherein R$_1$ and R$_2$ are independently selected from the group consisting of hydrogen and a lower alkyl group having between about one and six carbons;

wherein $R_3$ is selected from the group consisting of

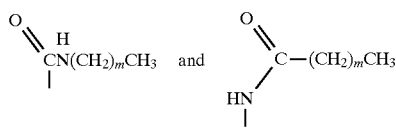 and 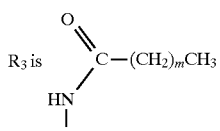

wherein m is between about 3 and 13; and
wherein X and Y are both carbons and the bond between X and Y is either single or double, except when

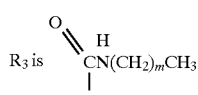

the bond between X and Y is single.

2. The compound of claim 1, wherein $R_1$ and $R_2$ are both hydrogen.

3. The compound of claim 2, wherein m is between 6 and 9.

4. The compound of claim 3, wherein

and the bond between X and Y is single.

5. The compound of claim 4, wherein m is equal to 6.

6. A method for therapeutically treating a patient to having an estrogen dependent illness comprising:

a) incorporating a compound having the formula

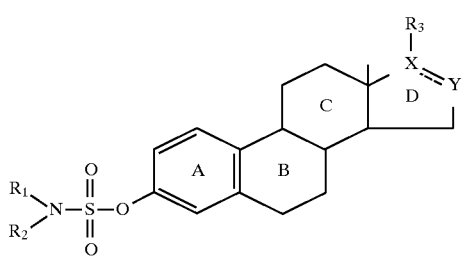

wherein $R_1$ and $R_2$ are independently selected from the group consisting of hydrogen and a lower alkyl group having between about one and six carbons;
wherein $R_3$ is selected from the group consisting of

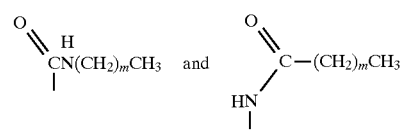

wherein m is between about 3 and 13; and
wherein X and Y are both carbons and the bond between X and Y is either single or double, except when

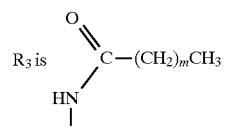

the bond between X and Y is single;
and
b) administering to said patient a therapeutically effective amount of the composition of step a).

7. The method of claim 6, including using a suitable pharmaceutical carrier selected from the group consisting of physiologic saline and 5% dextrose.

8. The method of claim 6, wherein said administration is parenteral.

9. The method of claim 6, including employing a compound wherein $R_1$ and $R_2$ are hydrogen;

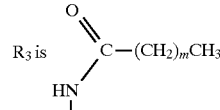

the bond between X and Y is single and m is equal to 6.

10. A method for prophylactically treating a patient having an estrogen dependent illness comprising:

a) incorporating a compound having the formula

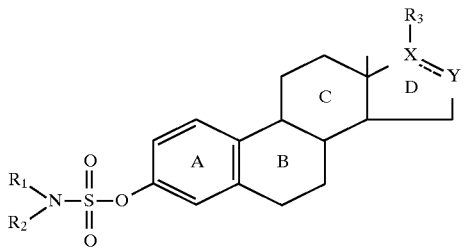

wherein $R_1$ and $R_2$ are independently selected from the group consisting of hydrogen and a lower alkyl group having between about one and six carbons; wherein $R_3$ is selected from the group consisting of

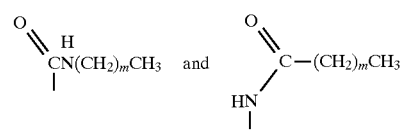

wherein m is between about 3 and 13;

wherein X and Y are both carbons and the bond between X and Y is either single or double, except when

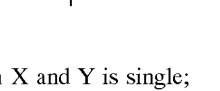

the bond between X and Y is single;
and
b) administering to said patient a prophylactically effective amount of the composition of step a).

11. The method of claim 10, including using a suitable pharmaceutical carrier selected from the group consisting of physiologic saline and 5% dextrose.

12. The method of claim 10, wherein said administration is parenteral.

13. The method of claim 10, including employing a compound wherein $R_1$ and $R_2$ are hydrogen;

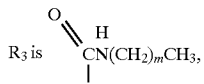

the bond between X and Y is single and m is equal to 6.

14. A method for preparing 17β-(N-alkylcarbamoyl)estra-1,3,5(10)triene-3-O-sulfamates comprising:
   a) mixing estrone with $(CF_3SO_2)_2O$ to form bis-triflate;
   b) mixing the bis-triflate of step a) with Palladium (II) acetate, triphenyl phosphine and n-alkylamine in a solvent and heating the mixture while bubbling carbon monoxide through the mixture;
   c) dissolving the product of step b) in a mixture of methanol and water;
   d) adding $K_2CO_3$ to the mixture of step c) and refluxing;
   e) adding NaH to a solution comprising the product of step d) in a solvent under nitrogen and stirring the mixture; and
   f) adding $ClSO_2NH_2$ to the mixture of step e).

15. The method of claim 14, further comprising:
   g) stirring a solution comprising the product of step f) in a mixture of EtOH and EtOAc with a catalyst under a hydrogen atmosphere for between 2 and 3 hours.

16. The method of claim 15, wherein the solvent in steps b) and e) is dimethylformamide, the catalyst of step g) is $PtO_2$ and the n-alkylamine of step b) has between 4 and 14 carbons.

17. A method for preparing 3-sulfamoyloxy-17β-octanoylamino-estra-1,3,5(10)-triene compounds comprising:
   a) mixing estrone with a $CH_3I$ and $K_2CO_3$ solution in acetone and refluxing the mixture for between about 60 and 80 hours;
   b) preparing a solution containing the product of step a) in tetrahydrofuran and methanol;
   c) adding sodium cyanoborohydride to the solution of step b) and mixing for between about 90 and 100 hours;
   d) mixing the product of step c) with triethylamine and dimethylamino pyridine;
   e) adding an alkanoyl chloride to the mixture of step d);
   f) mixing the product of step e) with $CH_2Cl_2$ and $BBr_3$ under nitrogen and stirring for between about 2 and 3 hours; and
   g) adding NaH and $ClSO_2NH_2$ to the product of step f) and stirring the mixture for between about 20 and 30 hours.

18. The method of claim 17, wherein the alkanoyl chloride of step e) has between about 5 and 15 carbons.

* * * * *

UNITED STATES PATENT AND TRADEMARK OFFICE
CERTIFICATE OF CORRECTION

PATENT NO. : 5,880,115

DATED : March 9, 1999

INVENTOR(S) : Li et al.

It is certified that errors appear in the above-identified patent and that said Letters Patent should be corrected as shown below:

Col. 5, line 15, the phrase "Sa-reductase" should read --5a-reductase--.

Col. 10, line 67, the phrase "having between about one and six" should read --having one to six carbons--

Col. 11, line 10, the phrase "m is between about 3 and 13" should read -- m is 3 to 13--, Col. 11, line 25, the phrase "m is between 6 and 9" should read --m is 6 to 9--, Col. 11, line 35, the phrase "wherein m is equal to 6" should read --wherein m is 6--;

Col. 11, line 37, the phrase "for therapeutically treating a patient to having an estrogen dependent illness comprising:", should read --of treating a patient for an estrogen dependent illness comprising administering to said patient a therapeutically effective amount of --

Col. 11, line 39, delete the phrase "a) incorporating"

Col. 11, line 54, the phrase "having between one and six carbons" should read --having one to six carbons--

UNITED STATES PATENT AND TRADEMARK OFFICE
CERTIFICATE OF CORRECTION

PATENT NO.    :    5,880,115

DATED         :    March 9, 1999

INVENTOR(S)   :    Li et al.

It is certified that errors appear in the above-identified patent and that said Letters Patent should be corrected as shown below:

Col. 11, line 65, the phrase "m is between about 3 and 13" should read --m is 3 to 13--

Col. 12, delete lines 10, 11 and 12, delete the ";" after "single" and replace with a --period (.)--

Col. 12, line 13, the phrase "including using a suitable" should read --including incorporating said compound into a suitable--

Col. 12, line 27, the phrase "estrogen dependent illness comprising:" should read --estrogen dependent illness comprising administering to said patient a prophylactically effective amount of--, Col. 12, line 28, delete the phrase "a) incorporating"

Col. 12, line 43, the phrase "having between about one and six carbons" has been changed to read having one to six carbons.--

Col. 12, line 52, the phrase "m is between about 3 and 13" has been changed to read --wherein m is 3 to 13--

Col. 12, delete lines 65, 66 and 67, delete the ";"after "single" and replace with a "period (.)"

UNITED STATES PATENT AND TRADEMARK OFFICE
CERTIFICATE OF CORRECTION

PATENT NO. : 5,880,115

DATED : March 9, 1999

INVENTOR(S) : Li et al.

It is certified that errors appear in the above-identified patent and that said Letters Patent should be corrected as shown below:

Col. 13, line 1, the phrase "including using a suitable" has been changed to —including incorporating said compound into a suitable--

Col. 13, line 13, the phrase "m is equal to 6" has been changed to —m is 6--

Col. 14, line 29, the phrase "has between about 5 and 15 carbons," has been changed to read —has 5 to 15 carbons--

Signed and Sealed this

Twelfth Day of September, 2000

Attest:

Q. TODD DICKINSON

*Attesting Officer*           *Director of Patents and Trademarks*